(12) United States Patent
Madore et al.

(10) Patent No.: US 11,744,558 B2
(45) Date of Patent: Sep. 5, 2023

(54) SYSTEMS AND METHODS FOR CONTROLLING IMAGING ARTIFACTS USING AN ARRAY OF SENSOR DATA

(71) Applicant: THE BRIGHAM AND WOMEN'S HOSPITAL, INC., Boston, MA (US)

(72) Inventors: Bruno Madore, Cambridge, MA (US); Frank R. Preiswerk, Cambridge, MA (US)

(73) Assignee: THE BRIGHAM AND WOMEN'S HOSPITAL, Boston, MA (US)

( * ) Notice: Subject to any disclaimer, the term of this patent is extended or adjusted under 35 U.S.C. 154(b) by 834 days.

(21) Appl. No.: 16/499,660

(22) PCT Filed: Mar. 31, 2018

(86) PCT No.: PCT/US2018/025602
§ 371 (c)(1),
(2) Date: Sep. 30, 2019

(87) PCT Pub. No.: WO2018/183982
PCT Pub. Date: Oct. 4, 2018

(65) Prior Publication Data
US 2020/0113546 A1    Apr. 16, 2020

Related U.S. Application Data

(60) Provisional application No. 62/598,561, filed on Dec. 14, 2017, provisional application No. 62/479,774, filed on Mar. 31, 2017.

(51) Int. Cl.
*A61B 8/00* (2006.01)
*A61B 5/055* (2006.01)
(Continued)

(52) U.S. Cl.
CPC .......... *A61B 8/5276* (2013.01); *A61B 5/0044* (2013.01); *A61B 5/055* (2013.01);
(Continued)

(58) Field of Classification Search
CPC ........ A61B 5/055; A61B 5/721; A61B 8/4477
See application file for complete search history.

(56) References Cited

U.S. PATENT DOCUMENTS

2014/0046188 A1* 2/2014 Yen ...................... G10K 11/346
600/447
2014/0275966 A1 9/2014 Schwartz
(Continued)

FOREIGN PATENT DOCUMENTS

DE    102005059211 A1    6/2007

OTHER PUBLICATIONS

Preiswerk et al., "Hybrid MRI-Ultrasound Acquisitions, and Scannerless Real-Time Imaging" Magnetic Resonance in Medicine 78: 897-908 (2017) (published online Oct. 13, 2016) (Year: 2016).*
(Continued)

*Primary Examiner* — Colin T. Sakamoto
(74) *Attorney, Agent, or Firm* — Quarles & Brady LLP (57) ABSTRACT

A system and method is provided for controlling against artifacts in medical imaging. The system includes an array of ultrasound sensors, each ultrasound sensor in the array of ultrasound sensors located at a variety of different spatial locations on a subject being imaged by an imaging system configured to generate medical imaging data and each ultrasound sensor configured to receive ultrasound sensor data. The system also includes a processor configured to receive the ultrasound sensor data from the array of ultrasound sensors, multiplex the ultrasound sensor data, generate anatomical information from the multiplexed ultrasound sensor data and correlated to the imaging system, and deliver
(Continued)

the anatomical information to the imaging system in a form for use by the imaging system to either acquire the imaging data using the anatomical information or reconstruct the imaging data using the anatomical information.

11 Claims, 6 Drawing Sheets

(51) Int. Cl.
    *A61B 6/00*     (2006.01)
    *A61B 8/08*     (2006.01)
    *A61B 5/00*     (2006.01)
    *A61N 5/10*     (2006.01)
    *A61B 6/03*     (2006.01)

(52) U.S. Cl.
    CPC ............ *A61B 5/721* (2013.01); *A61B 5/7289* (2013.01); *A61B 5/7292* (2013.01); *A61B 6/503* (2013.01); *A61B 6/527* (2013.01); *A61B 6/5288* (2013.01); *A61B 8/4416* (2013.01); *A61B 8/4477* (2013.01); *A61B 6/037* (2013.01); *A61B 6/5247* (2013.01); *A61N 2005/1058* (2013.01)

(56) References Cited

U.S. PATENT DOCUMENTS

2015/0164468 A1     6/2015     Ahn et al.
2015/0250450 A1     9/2015     Thomas

OTHER PUBLICATIONS

Wu P-H, et al. Hybrid MR-ultrasound acquisition for multi-baseline thermometry. ISMRM 25th Annual Meeting. 2017.
Zaitsev M, et al. Motion artifacts in MRI: A complex problem with many partial solutions. J Magn Reson Imaging 2015;42(4):887-901. PMCID:PMC4517972.
Automotive Sensors and Electronics Expo 2017 Conference webpage http://www.automotivesensors2017.com/.
Buonocore MH, et al. Ghost artifact reduction for echo planar imaging using image phase correction. Magn Reson Med 1997;38(1):89-100.
Chao TC, et al. A 2D MTF approach to evaluate and guide dynamic imaging developments. Magn Reson Med 2010;63(2):407-418.
Chao, TC, et al. "Fast diffusion imaging with high angular resolution." Magnetic resonance in medicine 77.2 (2017) 696-706.
Derbyshire JA, et al. Dynamic scan-plane tracking using MR position monitoring. J Magn Reson Imaging 1998;8 (4):924-932.
Feinberg DA, et al. Hybrid ultrasound MRI for improved cardiac imaging and real-time respiration control. Magn Reson Med 2010;63(2):290-296. PMCID:PMC2813925.
Frauenrath, T., et al. (2010). Acoustic cardiac triggering: a practical solution for synchronization and gating of cardiovascular magnetic resonance at 7 Tesla. Journal of Cardiovascular Magnetic Resonance, 12(1), 1.
Fraunhofer MEVIS. MR-compatible Ultrasound System and 3D Probe with real-time Tissue and Deformation Tracking. Webpage: https://www.mevis.fraunhofer.de/en/solutionpages/mr-compatible-ultrasound-system-and-3d-probe-with-real-time-tissue-and-deformation-tracking.html. Accessed on Nov. 8, 2019.
Glover GH. 3D z-shim method for reduction of susceptibility effects in BOLD fMRI. Magn Reson Med 1999;42 (2):290-299.
Grissom, W.A., et al., Hybrid referenceless and multibaseline subtraction MR thermometry for monitoring thermal therapies in moving organs. Medical physics, 2010. 37(9): p. 5014-5026.
Gunther M, et al. Ultrasound-guided MRI: preliminary results using a motion phantom. Magn Reson Med 2004;52 (1):27-32.

Hoge, WS. "A subspace identification extension to the phase correlation method [MRI application]." IEEE transactions an medical imaging 22.2 (2003): 277-280.
Hood MN, et al. Chemical shift: the artifact and clinical tool revisited. Radiographies 1999;19(2):357-371.
International Searching Authority, International Search Report and Written Opinion for application PCT/US2018/025602, dated Jun. 11, 2018.
Ishihara, Y., et al., A precise and fast temperature mapping using water proton chemical shift. Magn Reson Med, 1995. 34(6): p. 814-823.
Jehenson P, Syrota A. Correction of distortions due to the pulsed magnetic field gradient-induced shift in BO field by postprocessing. Magn Reson Med 1989;12(2):253-256.
Kuglin, C. D. "The phase correlation image alignment method." Proc. Int. Conference Cybernetics Society. 1975.; 163-165.
Lasso A, et al. PLUS: open-source toolkit for ultrasound-guided intervention systems. IEEE Trans Biomed Eng 2014;61(10):2527-2537.
Madore B, Glover GH, Pelc NJ. Unaliasing by Fourier-encoding the overlaps using the temporal dimension (UNFOLD), applied to cardiac imaging and fMRI. Magn Reson Med 1999;42:813-828.
Madore B. Unfold-Sense: a parallel MRI method with self-calibration and artifact suppression. Magn Reson Med 2004;52(2):310-320.
Mansfield P, Maudsley AA. Planar spin imaging by NMR. J Magn Reson 1977;27:101-119.
Mei CS, et al. Combining two-dimensional spatially selective RF excitation, parallel imaging, and UNFOLD for accelerated MR thermometry imaging. Magn Reson Med 2011;66(1):112-122.
Nakamura M, et al. Elevated antibodies to synthetic peptides of HTLV-1 envelope transmembrane glycoproteins in patients with HAM/TSP. J Neuroimmunol 1991;35(1-3):167-177.
OCMDemo—Github site online at https://github.com/fpreiswerk/OCMDemo. Last updated on Mar. 2, 2018.
O'Connor JM, et al. A method to synchronize signals from multiple patient monitoring devices through a single input channel for inclusion in list-mode acquisitions. Med Phys 2013;40(12):122502. PMCID:PMC3843760.
OECD (2019), Magnetic resonance imaging (MRI) exams (indicator), doi: 10.1787/1d89353f-en (Accessed on Nov. 8, 2019).
Oshinski, JN et al., Two-dimensional coronary MR angiography without breath holding., Radiology 1996 201:3, 737-743.
Pace OF, et al. An open-source real-time ultrasound reconstruction system for four-dimensional imaging of moving organs. Insight Journal 2009:1-8.
Panych, LP., et al. "Implementation of wavelet-encoded MR imaging." Journal of Magnetic Resonance Imaging 3.4 (1993): 649-655.
Petrusca L, et al. Hybrid ultrasound/magnetic resonance simultaneous acquisition and image fusion for motion monitoring in the upper abdomen. Invest Radial 2013;48(5):333-340.
Preiswerk F, et al. Ultrasound-based cardiac gating for MRI Proceedings of the International Society of Magnetic Resonance in Medicine. Honolulu, USA, 2017: p. 4443.
Preiswerk F, et al. Scannerless real-time MRI. International Society of Magnetic Resonance in Medicine. Proceedings of the International Society of Magnetic Resonance in Medicine. Singapore, 2016: p. 3578.
Preiswerk F, et al. Hybrid MRI-Ultrasound acquisitions, and scannerless real-time imaging. Magn Reson Med 2017;78(3):897-908. PMCID:PMC5391319.
Preiswerk F, et al. Hybrid Ultrasound and MRI Acquisitions for High-Speed Imaging of Respiratory Organ Motion. Medical Image Computing and Computer-Assisted Intervention—MICCAI 2015: Springer International Publishing; 2015. p. 315-322.
Preiswerk F, et al. RF-sensing for Trigger-based Synchronization of Auxiliary Devices, and Pulse-sequence Debugging. ISMRM 25th Annual Meeting. 2017.
Preiswerk F, et al. Speeding-up MR acquisitions using ultrasound signals, and scanner-less real-time MR imaging. Proceedings of the International Society of Magnetic Resonance in Medicine. Toronto, Canada, 2015: p. 0863.

(56) References Cited

OTHER PUBLICATIONS

Qian D, et al. An RF dosimeter for independent SAR measurement in MRI scanners. Med Phys 2013;40(12):122303. PMCID:PMC3843752.

Rieke, V., et al., Referenceless PRF shift thermometry. Magnetic resonance in medicine, 2004. 51(6): p. 1223-1231.

Schultz G, et al. Reconstruction of MRI data encoded with arbitrarily shaped, curvilinear, nonbijective magnetic fields. Magn Reson Med 2010;64{5}:1390-1403.

Schwartz BM, et al. Ultrasound echoes as biometric navigators. Magn Reson Med 2013;69(4):1023-1033.

Siemens Healthineers Biomatrix Sensors. Accessed online at https://usa.healthcare.siemens.com/magnetic-resonance-imaging/mri-technologies/biomatrix-sensors on Nov. 8, 2019.

Skope—Clip On Camera—accessed online at http://www.skope.swiss/clip-on-camera/—accessed on Nov. 8, 2019.

Spees WM et al., "Quantification and compensation of eddy-current-induced magnetic-field gradients." Journal of Magnetic Resonance 212.1 (2011): 116-123.

Stockmann JP, et al. 0-space imaging: Highly efficient parallel imaging using second-order nonlinear fields as encoding gradients with no phase encoding. Magn Reson Med 2010;64{2}:447-456. PMCID:PMC3147299.

Toews, M., et al. "Detecting rapid organ motion using a hybrid MR-ultrasound setup and Bayesian data processing." Proceedings of the International Society of Magnetic Resonance in Medicine. 2014.

Twieg DB. The k-trajectory formulation of the NMR imaging process with applications in analysis and synthesis of maging methods. Med Phys 1983;10(5):610-621.

Vannesjo, S. J., et al. "Field camera measurements of gradient and shim impulse responses using frequency sweeps." Magnetic resonance in medicine 72.2 (2014): 570-583.

Vigen, K.K., et al., Triggered, navigated, multi-baseline method for proton resonance frequency temperature mapping with respiratory motion. Magn Reson Med, 2003. 50(5): p. 1003-1010.

Wang Y, et al. Navigator-echo-based real-time respiratory gating and triggering for reduction of respiration effects in three-dimensional coronary MR angiography. Radiology 1996;198{1}:55-60.

Wedegaertner, U., et al. "A Novel Technique for Cardiac MRI of the Fetal Heart: MR compatible Doppler Ultrasound (CTG) for Cardiac Triggering." 2011 ISMRM.

Khatamian Y, et al. Significance and correction of respiratory off-resonance effects in fMRI-A phantom study. in Proc of Organization for Human Brain Mapping (OHBM). 2015; 1651.

\* cited by examiner

SYSTEMS AND METHODS FOR CONTROLLING IMAGING ARTIFACTS USING AN ARRAY OF SENSOR DATA

CROSS-REFERENCE TO RELATED APPLICATIONS

This application claims the benefit of U.S. Provisional Patent Application 62/479,774, filed Mar. 31, 2017, and entitled "MRI Sensors" and U.S. Provisional Patent Application 62/598,561, filed Dec. 14, 2017, and entitled "Ultrasound-based Sensors and Active Needles for Enhanced Medical Imaging and Therapy."

STATEMENT REGARDING FEDERALLY SPONSORED RESEARCH

This invention was made with government support under EB015898, and CA149342 awarded by the National Institutes of Health. The government has certain rights in the invention.

BACKGROUND

Image artifacts remain a prevalent limiting factor in a variety of imaging modalities, including magnetic resonance imaging (MRI) and tomographic imaging systems, such as positron emission tomography (PET) imaging systems, as well as other imaging systems. For example, in MRI and many other such imaging systems, scans may last several minutes, which presents an extended period during which even small movements by the patient can result in artifacts in the resulting images. As a result, in MRI alone, countless efforts have been made to address various types of patient motion, as well as other sources of errors, such as eddy currents, and the like. Motion-related problems also tend to plague other imaging modalities as well, such as PET Many motion correction efforts in MRI have relied upon special data acquisition or correction techniques using the MRI data itself, such as using navigators or techniques such as periodically rotated overlapping parallel lines with enhanced reconstruction (PROPELLER). However, some have attempted to use additional hardware to reduce or track patient motion. Examples include respiratory bellows or special, local motion-tracking coils. Thus, though avoiding additional/special hardware in the bore of an MRI system has often been preferred by many, such hardware systems have often been limited to devices such as respiration-monitoring belts, pulse oximeters, and electrocardiogram (ECG) leads, to help synchronize data acquisition with respiratory and cardiac motion. Other heavily researched devices aimed at monitoring physiological motion include digital stethoscopes, RF dosimeters, or Siemens' BioMatrix with an RF-based sensor in the patient table to detect changes in lung volume. The environment around the patient and the scanner itself can further be monitored in terms of oxygen levels, cryogen temperature, hardware temperature, transmitted/reflected power and dynamic electromagnetic field variations, for example With respect to cardiac imaging in particular, generating images that capture one or more specific cardiac phase(s) requires the active monitoring of cardiac activity as well as the synchronization of the imaging process to that activity. The standard for monitoring cardiac activity during cardiac imaging is electrocardiography (ECG), which senses the heart muscle's electrophysiological pattern using electrodes placed on the skin. However, depending on patient condition and scanner field strength, situations occur when ECG monitoring may not be a viable option. For example, in patients with prominent T waves, MRI acquisition may get erroneously triggered by T wave signals rather than by R waves. Alternately, the strength of the captured ECG signal may be impractically weak in some patients. Furthermore, ECG can get severely distorted due to the magnetohydrodynamic effect, especially at higher field strengths in MRI. Proposed alternatives to ECG include pulse gating which, although widely available, bears its own disadvantages mainly caused by the time delay required for a pressure wave to make its way from the heart to the hand. With respect to respiration-related motion during imaging, scanners are typically capable of adapting their acquisition process in a manner that minimizes deleterious effects, given they are provided with appropriate information about the motion. Such information may typically come from one or more respiratory bellows, navigator echoes and/or optical tracking of body contours.

Although previous sensors have alleviated some of the previous shortcomings present in imaging systems, there remains a need for new sensor innovations capable of improving image quality, particularly with respect to correcting image artifacts.

SUMMARY OF THE DISCLOSURE

The present disclosure addresses the aforementioned drawbacks by providing a system of ultrasound sensors capable of gathering anatomical information that can be used to reduce image artifacts. A plurality of single-element ultrasound sensors may be used to capture information with high temporal resolution from different vantage points on the body, which can be aggregated to provide patient motion or other information for error correction in data acquisition and reconstruction. This information can be incorporated into the image reconstruction process, and as a result, improve image quality.

In accordance with one aspect of the disclosure, a system is provided for controlling against artifacts in medical imaging. The system includes an array of ultrasound sensors, each ultrasound sensor in the array of ultrasound sensors located at a variety of different spatial locations on a subject being imaged by an imaging system configured to generate medical imaging data and each ultrasound sensor configured to receive ultrasound sensor data. The system also includes a processor configured to receive the ultrasound sensor data from the array of ultrasound sensors, multiplex the ultrasound sensor data, generate anatomical information from the multiplexed ultrasound sensor data and correlated to the imaging system, and deliver the anatomical information to the imaging system in a form for use by the imaging system to either acquire the imaging data using the anatomical information or reconstruct the imaging data using the anatomical information.

In accordance with another aspect of the disclosure, a method is provided for controlling operation of an imaging system to perform a medical imaging study. The method includes receiving ultrasound sensor data acquired using a plurality of multiplexed ultrasound sensors located at a variety of different spatial locations on a subject during performance of the medical imaging study using the medical imaging system. The method also includes generating anatomical information from the ultrasound sensor data and using the anatomical information to improve images produced by the imaging system during the imaging study.

In accordance with yet another aspect of the disclosure, a system is provided for real-time correction of imaging artifacts in an imaging system. The system includes an ultrasound sensor located on a torso of a subject and configured to receive ultrasound sensor data, a complementary sensor located on the subject and configured to receive complementary data, and a processor. The processor is configured to generate anatomical information correlated to an imaging system from the ultrasound sensor data and the complementary data, wherein the anatomical data comprises motion information of the subject. The processor is also configured to deliver the anatomical information into the imaging system to improve images produced by the imaging system.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention.

BRIEF DESCRIPTION OF THE DRAWINGS

FIG. 6B is a series of images that depict an experimental ultrasound sensor construction showing a 3D-printed holder designed to accommodate the transducer and ultrasound gel in an exploded view.

FIG. 6C is a series of images showing one side of the sensor closed by a thin membrane that is substantially transparent to ultrasound energy but capable of containing the ultrasound gel.

FIG. 6D is a series of images showing the sensor of FIG. 6C enclosed by twisting a lid, which was designed to apply pressure on the transducer, thus pushing it onto the skin.

FIG. 6E is an image showing a two-way tape that allows the sensor of FIGS. 6C and 6D to be fixed onto the skin.

DETAILED DESCRIPTION

Figure 1:
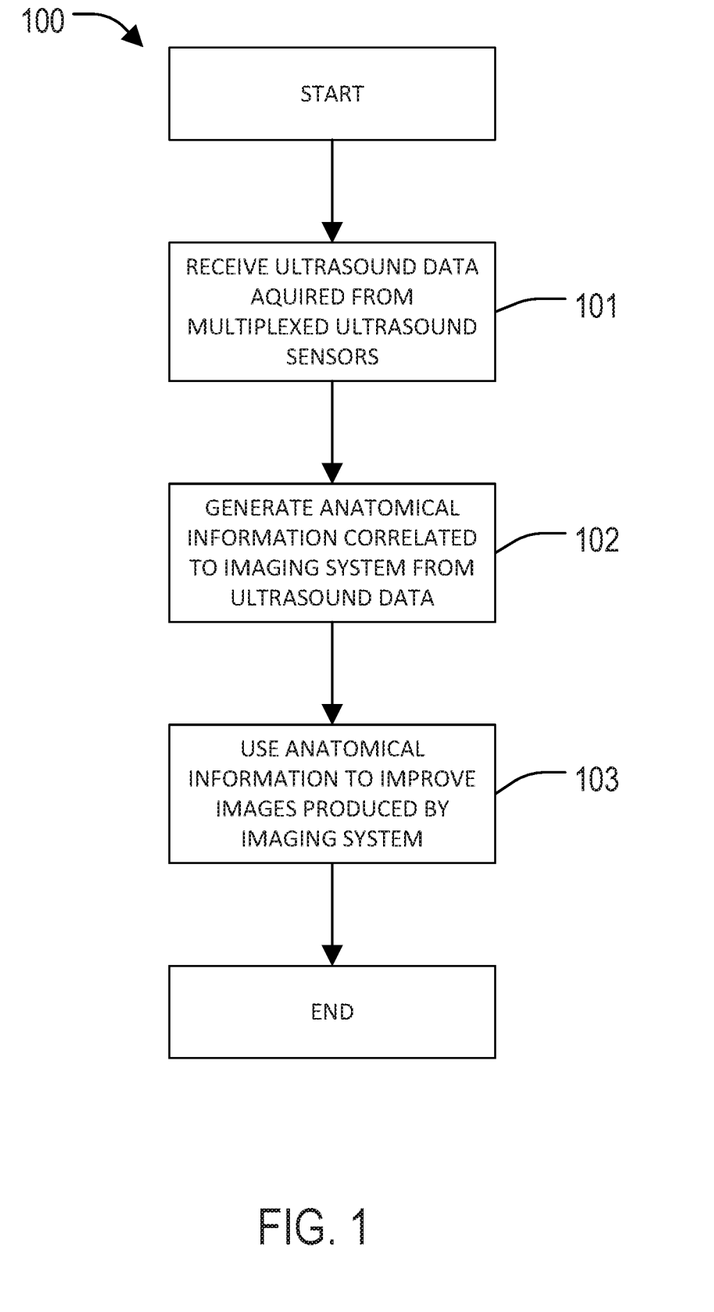
FIG. 1 depicts a method flowchart of a method for controlling imaging artifacts in an imaging system in accordance with present disclosure.

FIG. 1 depicts a method flowchart 100 of one non-limiting example of a method for correction of imaging data acquired using an imaging system. A first step includes receiving ultrasound sensor data acquired using a plurality of ultrasound sensors 101. As will be described, the plurality of ultrasound sensors may be multiplexed. As used herein, "multiplexing" may include processing the data from a plurality of individual sensors to generate a common or otherwise coherent set of data. For example, multiplexing may include the combination of multiple signals into a single transmission circuit or channel. For example, multiplexed sensors may have many sensors per connection line.

The next step may include generating anatomical information correlated to an imaging system from the ultrasound sensor data 102. Then the next step may include providing the anatomical information to the medical imaging system or otherwise using the anatomical information to improve images produced by the imaging system 103. In the method, the ultrasound sensors may be located at a variety of different spatial locations on a subject. Further, the imaging system of the method may be an MRI scanner, a PET scanner or an ultrasound imaging system, for example.

Although not depicted in FIG. 1, the method may include a step of receiving complementary data. Such complementary data may be acquired by a complementary sensor, which may include one or more electrocardiogram sensors or other, ultrasound or non-ultrasound sensors. With this additional data present, the anatomical information may be generated using both the non-ultrasound data and the ultrasound sensor data. The anatomical information may include cardiac cycle information of the subject. For example, the anatomical information may provide heartbeat frequency information to the imaging system. Regardless of the particular data acquired, this anatomical information may be provided in real-time while the imaging system is imaging the subject in accordance with an imaging study by the imaging system.

Figure 2:
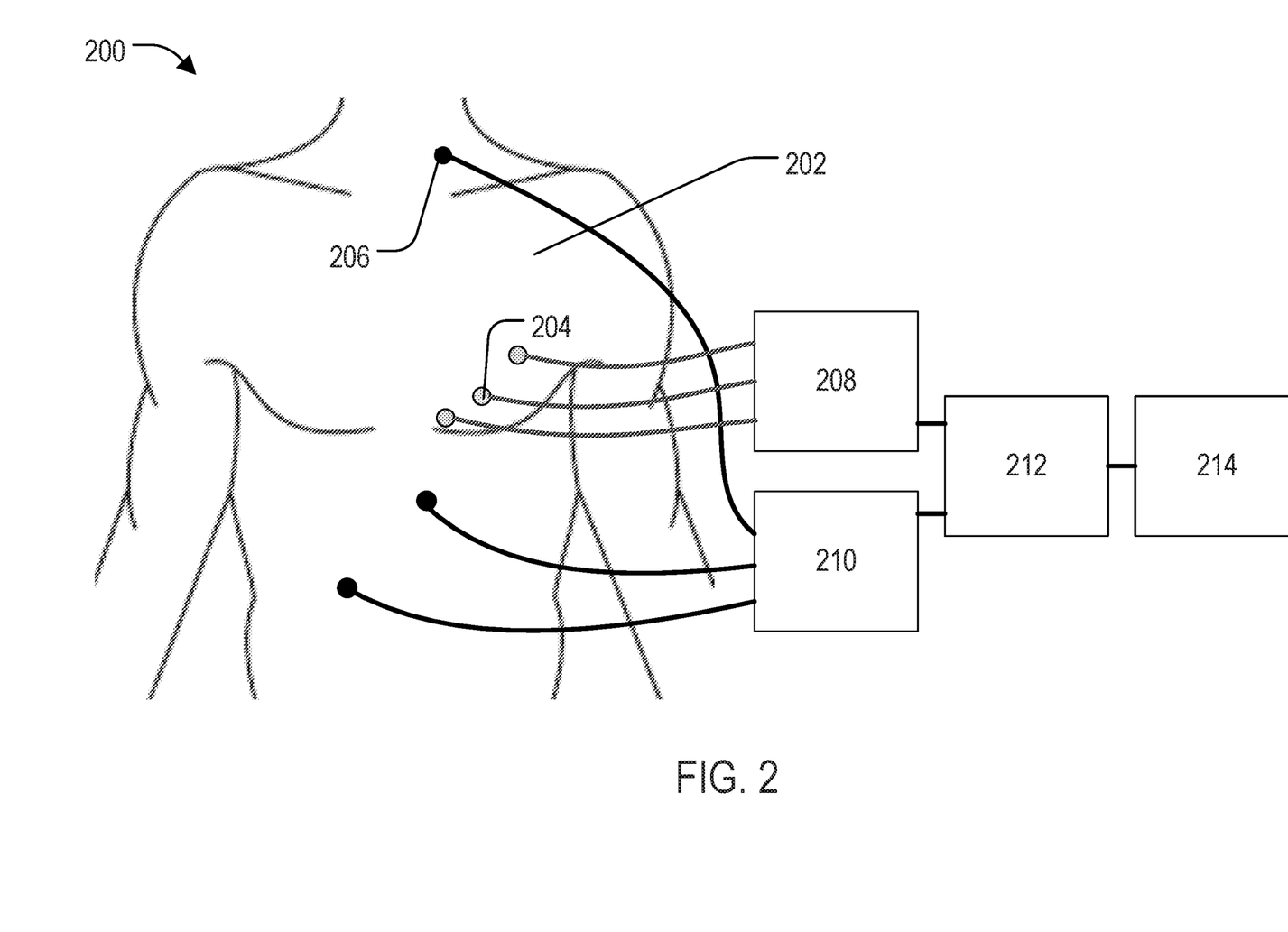
FIG. 2 depicts a system for controlling imaging artifacts in an imaging system in accordance with present disclosure.

FIG. 2 depicts a system 200 for prevention of imaging artifacts in an imaging system. The system is illustrated as deployed into one non-limiting clinical application related to an imaging study focused on the chest and, more particular, a cardiac-related study. In this way, the system 200 includes one or more ultrasound sensor(s) 204 located on a chest of a subject 202 and configured to receive ultrasound sensor data. The sensors can be compact, about 3×3×1 cm in size, and facilitate rapid application to the subject, such as by using a protective layer of tape that is simply peeled and the sensor is applied to the skin. Further, optional complementary sensors 206 may be included. The complementary sensors may, as a non-limiting example include electrocardiogram sensors, may be located at a variety of locations on subject 202, and are configured to receive complementary data. Electrically connected to the ultrasound sensor(s) 204 is an ultrasound controller 208. Electrically connected to the complementary sensors 206 is a complementary controller 210. The ultrasound controller 208 and the complementary controller 210 are electrically connected to a processor 212 and an imaging system 214. The processor 212 is configured to generate anatomical information correlated to the imaging system 214 from the ultrasound sensor data and the complementary data, wherein the anatomical data may comprise cardiac cycle information or respiration-related information of the subject. Once the anatomical information is generated, the processor 212 may deliver the anatomical information to the imaging system 214 in order to improve the resulting images created by the imaging system 214, such as by preventing motion artifacts that would otherwise be inherent in the imaging data acquired by the imaging system 214.

Although depicted as separate components, the ultrasound controller 208 and the complementary controller 210 may be located within the same housing, and may likewise be combined with the processor 212. In such a combined configuration, the ultrasound controller 208 and complementary controller 210 may be considered components of the processor 212. The ultrasound controller may include an ultrasound pulser and receiver. The electrocardiograph controller may include components present within a traditional ECG trigger box. The elements of the system may alternatively be connected wirelessly. Further, as will be explained, though the ultrasound sensors 204 are illustrated as multiple sensors, they may be replaced with or reflect a single sensor 204.

Figure 3:
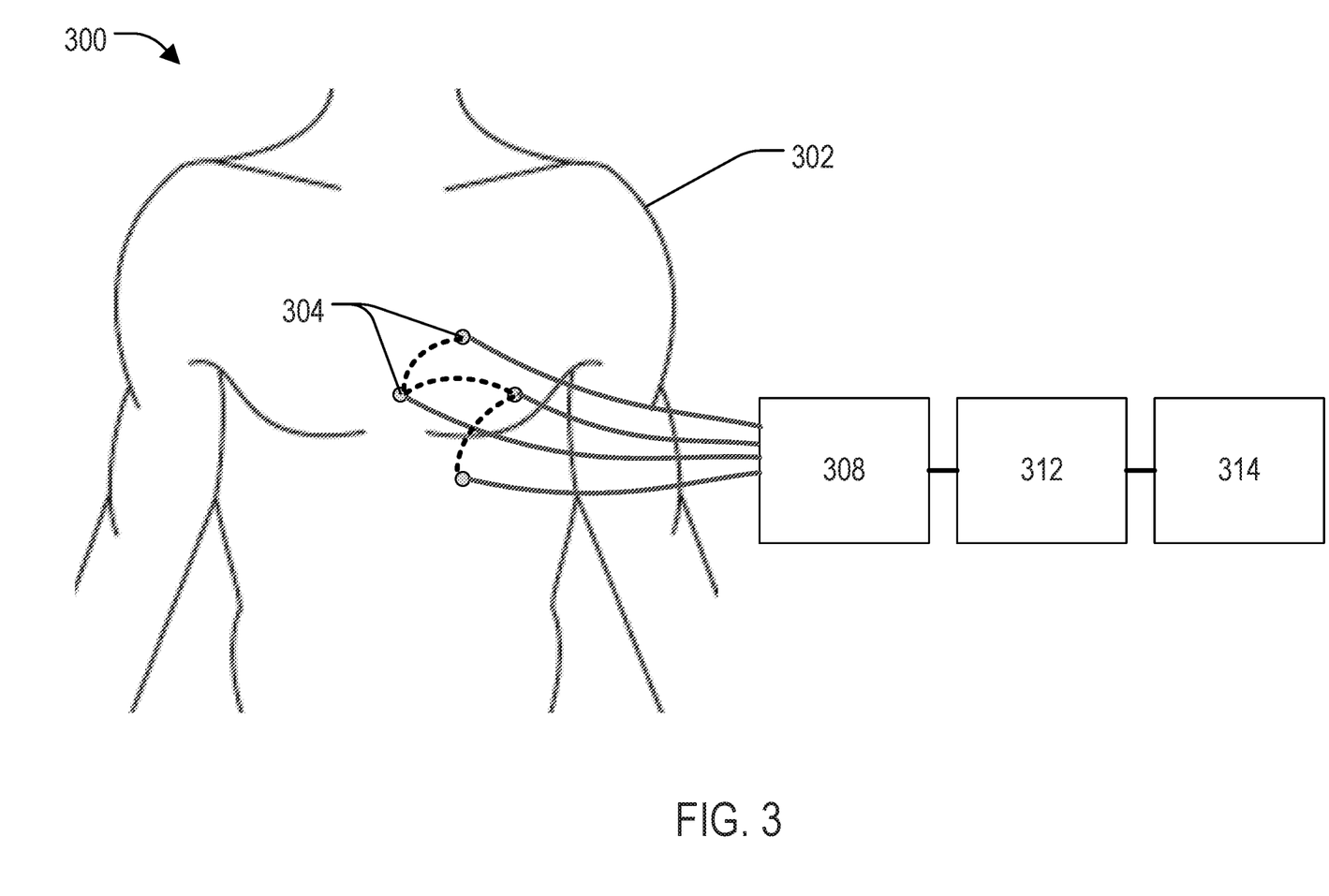
FIG. 3 depicts another system for controlling against imaging artifacts in an imaging system in accordance with present disclosure.

Specifically, FIG. 3 depicts another system 300 for real-time correction of imaging data acquired by an imaging system. The system includes an array of multiplexed ultrasound sensors 304 located at a variety of different spatial locations on a subject 302 and configured to receive ultrasound sensor data. Electrically connected to the ultrasound sensor 304 is an ultrasound controller 308. The sensors may be connected in parallel, as illustrated, or in series, as illustrated with the optional, dashed lines. A processor 312 is configured to multiplex the ultrasound sensor data, generate anatomical information correlated to an imaging system 314 from the multiplexed ultrasound sensor data, and deliver the anatomical information into the imaging system 314 to control artifacts and improve images. Alternatively, the anatomical or even raw imaging information may be provided to an image reconstruction system that may be separate from the imaging system 314.

Although depicted as a separate component, the ultrasound controller 308 may be located within the same housing as the processor 312. In such a combined configuration, the ultrasound controller 308 may be considered a component of the processor 312. The ultrasound controller may include an ultrasound pulser and receiver. The elements of the system may alternatively be connected wirelessly.

The system of FIG. 3 may also include one or more complementary sensors configured to receive complementary data. Similar to FIG. 2, these complementary sensors may be electrically connected to a complementary controller which may be considered a component of the processor. The complementary sensors may provide complementary data which can be used with the multiplexed ultrasound sensor data to generate the anatomical information.

The ultrasound sensors implemented in the systems and methods described herein may be single-element ultrasound-based sensors, also referred to as 'Organ Configuration Motion' (OCM) sensors, which may gather motion-related information during MRI acquisitions. While traditional ultrasound scanners generate ultrasound images, OCM sensors do not generate images, but instead generate a signal with a magnitude and phase that is sensitive to motion and organ position. The beam measured by each of these single-element ultrasound sensors may be unfocused and reflected multiple times; however, focused ultrasound may be used. Especially when using unfocused ultrasound, signals may come from a variety of directions and paths within the subject. This unique characteristic can create a richness and complexity of the OCM signals, making them effective "code words" for 3D organ configuration. As time-matched OCM signals and imaging system images are acquired, correlations between the two can be used to correct the acquired imaging data from the imaging system or to control the imaging system to reduce or avoid acquiring data that result in images having substantial artifacts, such as motion artifacts.

Each ultrasound sensor may include an ultrasound transducer capable of both transmitting and receiving ultrasound signals. Each of these transducers may be enclosed within a sensor housing. Each ultrasound sensor may also include an ultrasound gel. Each ultrasound sensor may include a membrane transparent to ultrasound energy but capable of containing the ultrasound gel. Each ultrasound sensor may include adhesive material for fixation onto the skin. Each ultrasound sensor may also include a temperature probe. The sensor housing may be 3D printed. The ultrasound sensors may be multiplexed. There may be multiple signal lines connected to the ultrasound controller and the processor, each signal line containing numerous multiplexed US sensors.

The multiplexed ultrasound sensors may be located at a variety of different spatial locations on the subject. For example, these spatial locations may be on the head, neck, chest, or stomach of the subject. The exact positioning of each sensor depends on the intended region to be imaged, and the type of artifacts to be controlled, such as to reduce or present against. Each ultrasound sensor may have a minimum spatial distance of about 0.5, 1, 2, 3, 4, or 5 inches from any adjacent sensor. The sensors may directly contact the skin of the subject or indirectly contact the subject through a media. The sensors may be adhesively attached to the skin. The ultrasound sensors may be attached to a substrate configured to maintain spatial distances between each US sensor. For example, the sensors may be attached to a fabric or garment. Although the anatomical information is often described as relating to cardiac induced motion, anatomical motion such as respiratory motion, bowel movements, as well as other internal motion within the subject may be measured.

The processor of the systems and methods described herein may be configured to generate and input anatomical information into the imaging system. The processor may use a Bayesian, kernel density estimation, or deep learning algorithm or comparable processing technique to generate the anatomical information. The processor may be small enough to fit into a 1 ft×1 ft×1 ft box or a 0.5 ft×0.5 ft×0.5 ft box. The processor may input the anatomical information into the imaging system in a format that is already used by the imaging system to process images. This input format may vary depending on the maker of the commercial imaging system.

The imaging system to which the anatomical information is provided may be a magnetic resonance imaging or tomographic imaging system. For example, the imaging system may be a computed tomography (CT), positron emission tomography (PET), or a single photon emission computed tomography (SPECT) system. Also, the imaging system may be part of an imaging system for performing a therapy, such as radiation or particle or proton therapy.

Figure 4:
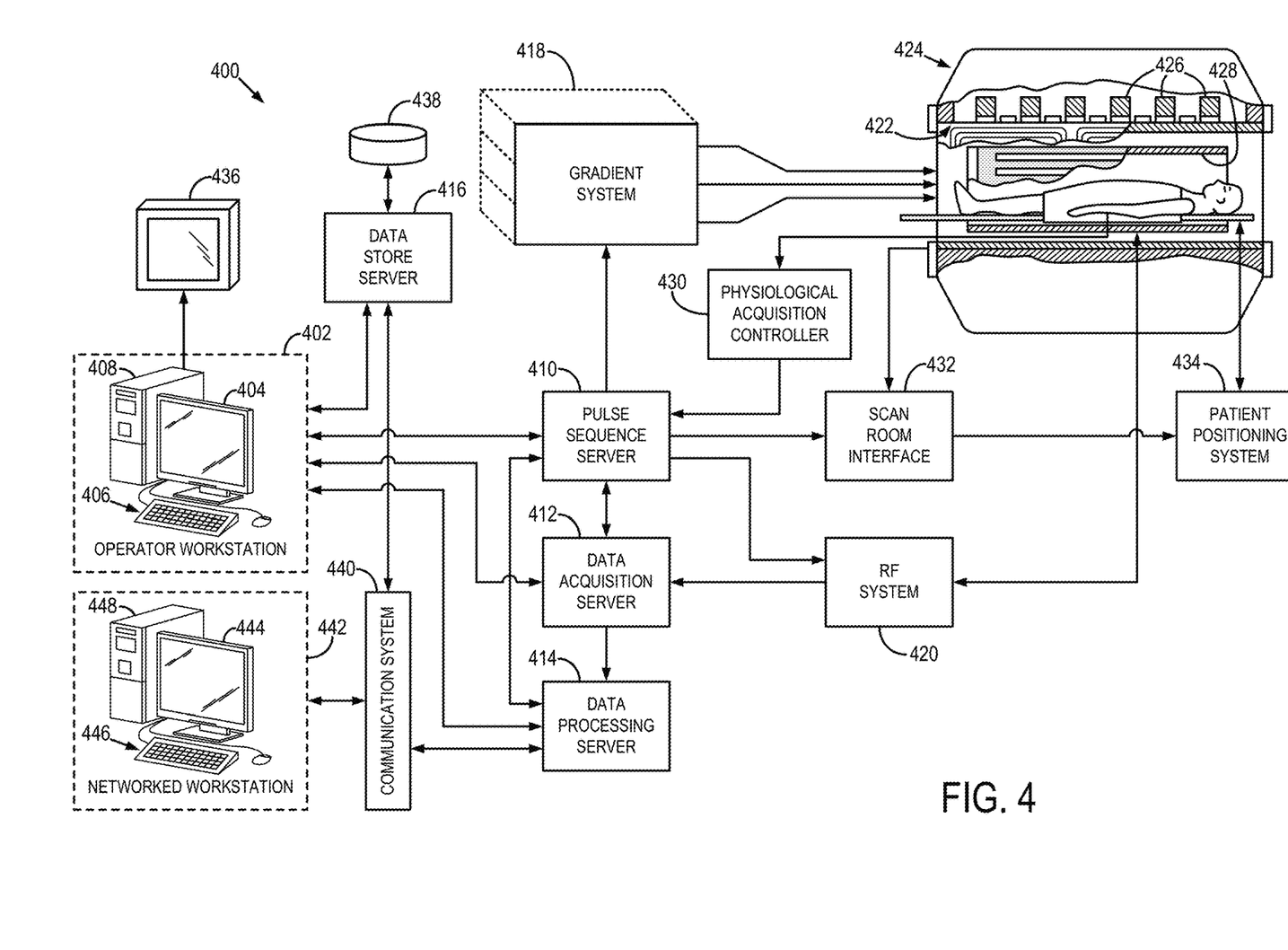
FIG. 4 depicts a block diagram of an example magnetic resonance imaging ("MRI") system that can implement the systems and methods of the present disclosure.

Referring particularly now to FIG. 4, an example of a magnetic resonance imaging ("MR") or nuclear magnetic resonance (NMR) system 400 that can implement the systems and methods described herein is illustrated. The MR system 400 includes an operator workstation 402 that may include a display 404, one or more input devices 406 (e.g., a keyboard, a mouse), and a processor 408. The processor 408 may include a commercially available programmable machine running a commercially available operating system. The operator workstation 402 provides an operator interface that facilitates entering scan parameters into the MR system 400. The operator workstation 402 may be coupled to different servers, including, for example, a pulse sequence server 410, a data acquisition server 412, a data processing server 414, and a data store server 416. The operator workstation 402 and the servers 410, 412, 414, and 416 may be connected via a communication system 440, which may include wired or wireless network connections.

The pulse sequence server 410 functions in response to instructions provided by the operator workstation 402 to operate a gradient system 418 and a radiofrequency ("RF")

system 420. Gradient waveforms for performing a prescribed scan are produced and applied to the gradient system 418, which then excites gradient coils in an assembly 422 to produce the magnetic field gradients $G_x$, $G_y$, and $G_z$ that are used for spatially encoding magnetic resonance signals. The gradient coil assembly 422 forms part of a magnet assembly 424 that includes a polarizing magnet 426 and a whole-body RF coil 428.

RF waveforms are applied by the RF system 420 to the RF coil 428, or a separate local coil to perform the prescribed magnetic resonance pulse sequence. Responsive magnetic resonance signals detected by the RF coil 428, or a separate local coil, are received by the RF system 420. The responsive magnetic resonance signals may be amplified, demodulated, filtered, and digitized under direction of commands produced by the pulse sequence server 410. The RF system 420 includes an RF transmitter for producing a wide variety of RF pulses used in MR pulse sequences. The RF transmitter is responsive to the prescribed scan and direction from the pulse sequence server 410 to produce RF pulses of the desired frequency, phase, and pulse amplitude waveform. The generated RF pulses may be applied to the whole-body RF coil 428 or to one or more local coils or coil arrays.

The RF system 420 also includes one or more RF receiver channels. An RF receiver channel includes an RF preamplifier that amplifies the magnetic resonance signal received by the coil 428 to which it is connected, and a detector that detects and digitizes the I and Q quadrature components of the received magnetic resonance signal. The magnitude of the received magnetic resonance signal may, therefore, be determined at a sampled point by the square root of the sum of the squares of the I and Q components:

$$M=\sqrt{I^2+Q^2} \tag{1}$$

and the phase of the received magnetic resonance signal may also be determined according to the following relationship:

$$\varphi = \tan^{-1}\left(\frac{Q}{I}\right). \tag{2}$$

The pulse sequence server 410 may receive patient data from a physiological acquisition controller 430. By way of example, the physiological acquisition controller 430 may receive signals from a number of different sensors connected to the patient, including electrocardiograph ("ECG") signals from electrodes, or respiratory signals from a respiratory bellows or other respiratory monitoring devices. These signals may be used by the pulse sequence server 410 to synchronize, or "gate," the performance of the scan with the subject's heart beat or respiration.

The pulse sequence server 410 may also connect to a scan room interface circuit 432 that receives signals from various sensors associated with the condition of the patient and the magnet system. Through the scan room interface circuit 432, a patient positioning system 434 can receive commands to move the patient to desired positions during the scan.

The digitized magnetic resonance signal samples produced by the RF system 420 are received by the data acquisition server 412. The data acquisition server 412 operates in response to instructions downloaded from the operator workstation 402 to receive the real-time magnetic resonance data and provide buffer storage, so that data is not lost by data overrun. In some scans, the data acquisition server 412 passes the acquired magnetic resonance data to the data processor server 414. In scans that require information derived from acquired magnetic resonance data to control the further performance of the scan, the data acquisition server 412 may be programmed to produce such information and convey it to the pulse sequence server 410. For example, during pre-scans, magnetic resonance data may be acquired and used to calibrate the pulse sequence performed by the pulse sequence server 410. As another example, navigator signals may be acquired and used to adjust the operating parameters of the RF system 420 or the gradient system 418, or to control the view order in which k-space is sampled. In still another example, the data acquisition server 412 may also process magnetic resonance signals used to detect the arrival of a contrast agent in a magnetic resonance angiography ("MRA") scan. For example, the data acquisition server 412 may acquire magnetic resonance data and processes it in real-time to produce information that is used to control the scan.

The data processing server 414 receives magnetic resonance data from the data acquisition server 412 and processes the magnetic resonance data in accordance with instructions provided by the operator workstation 402. Such processing may include, for example, reconstructing two-dimensional or three-dimensional images by performing a Fourier transformation of raw k-space data, performing other image reconstruction algorithms (e.g., iterative or back projection reconstruction algorithms), applying filters to raw k-space data or to reconstructed images, generating functional magnetic resonance images, or calculating motion or flow images.

Images reconstructed by the data processing server 414 are conveyed back to the operator workstation 402 for storage. Real-time images may be stored in a data base memory cache, from which they may be output to operator display 402 or a display 436. Batch mode images or selected real time images may be stored in a host database on disc storage 438. When such images have been reconstructed and transferred to storage, the data processing server 414 may notify the data store server 416 on the operator workstation 402. The operator workstation 402 may be used by an operator to archive the images, produce films, or send the images via a network to other facilities.

The MR system 400 may also include one or more networked workstations 442. For example, a networked workstation 442 may include a display 444, one or more input devices 446 (e.g., a keyboard, a mouse), and a processor 448. The networked workstation 442 may be located within the same facility as the operator workstation 402, or in a different facility, such as a different healthcare institution or clinic.

The networked workstation 442 may gain remote access to the data processing server 414 or data store server 416 via the communication system 440. Accordingly, multiple networked workstations 442 may have access to the data processing server 414 and the data store server 416. In this manner, magnetic resonance data, reconstructed images, or other data may be exchanged between the data processing server 414 or the data store server 416 and the networked workstations 442, such that the data or images may be remotely processed by a networked workstation 442.

Figure 5:
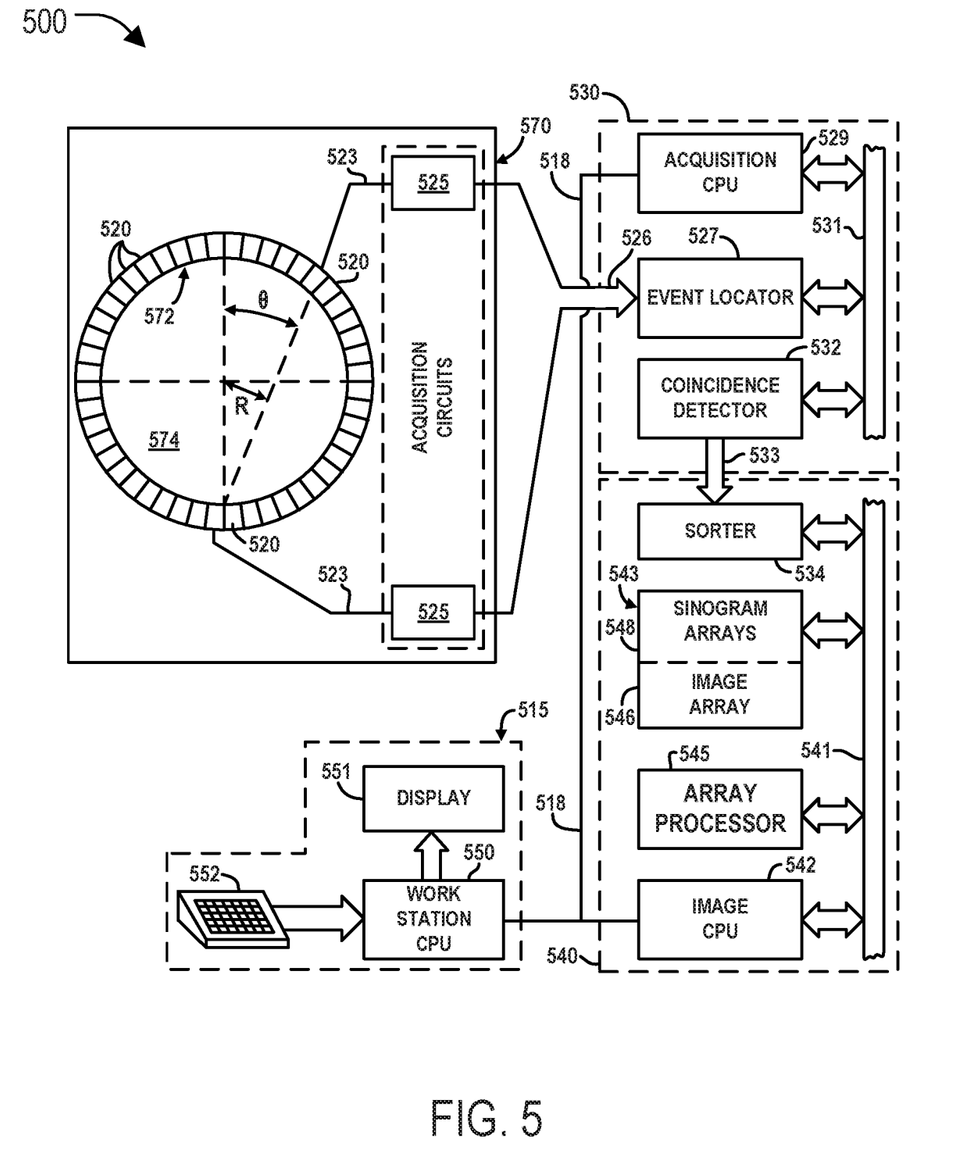
FIG. 5 depicts a block diagram of an example positron emission tomography ("PET") system that can implement the systems and methods of the present disclosure.
Figure 6A:
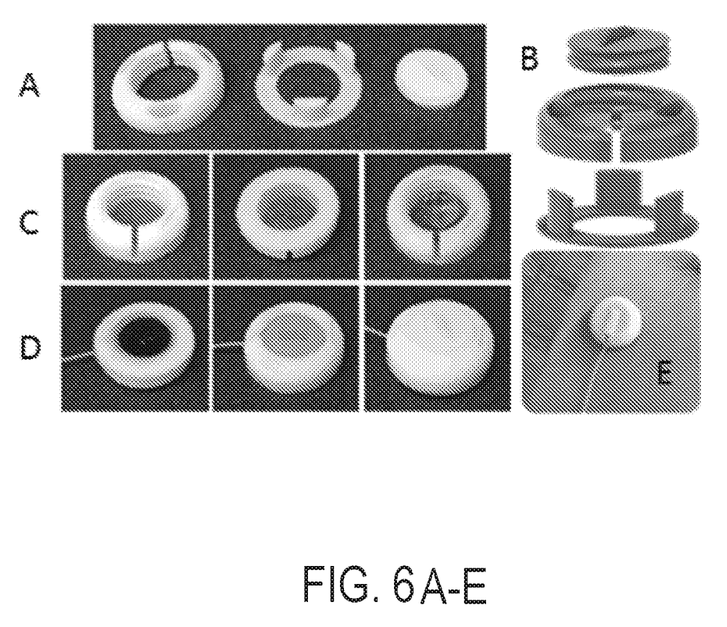
FIG. 6A is a series of images that depict an experimental ultrasound sensor construction showing a 3D-printed holder designed to accommodate the transducer and ultrasound gel.

Referring particularly now to FIG. 5, an example of a positron emission tomography (PET) system 500 that can implement the systems and methods described herein is illustrated. The PET scanner system 500 includes the gantry 570 which supports the detector ring assembly 572 within the cylindrical bore of the general magnet assembly. The detector ring 572 is comprised of detector units 520. Signals obtained are sent through a cable 526 to an event locator circuit 527 housed in a separate cabinet. Each acquisition circuit 525 also produces an event detection pulse (EDP) which indicates the exact moment the scintillation event took place.

The event locator circuits 527 form part of a data acquisition processor 530 which periodically samples the signals produced by the acquisition circuits 525. The processor 530 has an acquisition CPU 529 which controls communications on local area network 518 and a backplane bus 531. The event locator circuits 527 assemble the information regarding each valid event into a set of digital numbers that indicate precisely when the event took place and the position of the scintillator crystal which detected the event. This event data packet is conveyed to a coincidence detector 532 which is also part of the data acquisition processor 530.

The coincidence detector 532 accepts the event data packets from the event locators 527 and determines if any two of them are in coincidence. Coincidence is determined by a number of factors. First, the time markers in each event data packet must be within a preset time of each other, and second, the locations indicated by the two event data packets must lie on a straight line which passes through the field of view (FOV) in the bore of the magnet assembly. Events which cannot be paired are discarded, but coincident event pairs are located and recorded as a coincidence data packet.

The coincidence data packets are saved until a set of corrective values are received from the MRI system that reflect the current position of the subject. Using this corrective information and the information in each coincidence data packet, a corresponding set of corrected coincidence data packets is calculated. Each coincidence data packet is thus corrected to change its projection ray, (R, θ) by an amount corresponding to the movement of the subject away from the reference position.

The corrected coincidence data packets are conveyed through a link 533 to a sorter 534 where they are used to form a sinogram. This corrective process is repeated each time corrective values are received from the MRI system. The correction is made on those coincidence data packets that have accumulated since the receipt of the previous corrective values.

The sorter 534 forms part of an image reconstruction processor 540. The sorter 534 counts all events occurring along each projection ray (R, θ) and organizes them into a two dimensional sinogram array 548 which is stored in a memory module 543. In other words, a count at sinogram location (R, θ) is increased each time a corrected coincidence data packet at that projection ray is received. Due to the corrections made to the coincidence events, the sinogram that is formed during the scan depicts the subject being examined in the reference position despite subject motion that occurs during the scan. The image reconstruction processor 540 also includes an image CPU 542 that controls a backplane bus 541 and links it to the local area network 518. An array processor 545 also connects to the backplane 541 and it reconstructs an image from the sinogram array 548. The resulting image array 546 is stored in memory module 543 and is output by the image CPU 542 to the operator work station 515.

The operator work station 515 includes a CPU 550, a CRT display 551 and a keyboard 552. The CPU 550 connects to the local area network 518 and it scans the keyboard 552 for input information. Through the keyboard 552 and associated control panel switches, the operator can control the calibration of the PET scanner and its configuration. Similarly, the operator can control the display of the resulting image on the CRT display 551 and perform image enhancement functions using programs executed by the work station CPU 550.

EXAMPLES

The following non-limiting examples are provided in order to demonstrate and further illustrate certain embodiments and aspects of the present disclosure and are not to be construed as limiting the scope of the disclosure.

Example 1

A study was conducted to investigate the use of a custom 1 MHz single-element ultrasound (US) transducer, referred to here as an organ-configuration motion (OCM) sensor, for echocardiography-based cardiac MR-triggering. The sensor was placed over the heart, and the resulting signal was processed to generate triggers at the end of atrial systole, at the onset of isovolumic contraction. The device is MR compatible and can replace ECG gating when the latter proves impractical, for the purpose of cardiac MRI.

As shown in FIGS. 6A-E, the sensor is assembled from a 3D printed capsule of our own design, an MR-compatible 1 MHz US transducer, two-way tape, ultrasound gel and a membrane mostly transparent to ultrasound energy. Application to the skin can be done very easily: one peels the protective layer of the tape and applies the sensor onto the skin. Making the OCM sensors as easy to use as possible is important, as it may prove crucial to future clinical adoption. Our OCM sensors can be as easy to install as an ECG lead using a simple 'peel-and-apply' process.

A switching circuit allows switching between several OCM sensors. In other words, several OCM sensors can be placed on the torso of a given patient, providing the ability to compare signals from different locations and detect several different types of motion as monitored from different vantage points.

Eight volunteers were imaged following informed consent using a version of our OCM+MRI setup. The OCM sensor involved an MR-compatible transducer from Imasonics, 8 mm diameter, 5.0 MHz. The device was placed on the abdomen of the subject and Neoptix ReFlex fiberoptic temperature probes (Qualitrol Company LLC of Fairport, N.Y.) were employed to monitor any potential heating, for safety purposes. Scanning would have been stopped if the temperature of the device had exceeded body temperature (threshold at 38° C.). The OCM sensor was fired using an Olympus 5072PR pulser receiver (Olympus, Waltham, Mass.), as triggered by the MRI pulse sequence. Firings of the OCM sensor occurred outside of MR readout windows to avoid image artifacts.

The results showed that, once correlations were learned between MR images and OCM signals, then synthetic MR images could be generated on the basis of OCM signals alone, at the relatively high temporal resolution of the OCM acquisition.

Example 2

Simultaneous ultrasound and ECG sensor acquisition was studied. For the ultrasound sensors, a pulser-receiver (5077PR, Olympus) triggered the 1 MHz transducer at a pulse repetition frequency of 100 Hz. The signal was recorded using a standard PC equipped with a digitizer card (5122, National Instruments), acquiring 5000 samples at 20 MS/s, for a maximum depth of 19.25 cm. The ultrasound sensor was attached to the chest, directly over the heart. Three ECG leads were placed in the standard manner. Simultaneous OCM and ECG data were acquired, with the volunteer outside and then inside the 3T scanner, for 2 minutes each. The R-wave detection algorithm of the scanner, as applied to the minimally-distorted ECG traces acquired outside the bore, produced ground truth for validation purposes. A learning-based algorithm detected each heartbeat as follows. 200 OCM samples were selected around a depth of 16.5 cm. The mean absolute difference between subsequent OCM traces was used as a feature for heartbeat detection:

$$F(t) = \frac{\sum_{i=1}^{200} OCM_t(i) - OCM_{t-1}(i)}{200}; \quad (3)$$

where $OCM_t(i)$ is the ith data point acquired as part of the firing of an OCM sensor performed at time t. There may typically be 20,000 data points acquired per firing, over a period of roughly 0.2 ms, and such firings can be repeated very often, typically hundreds of times per second.

From the first 10 seconds, the standard deviation a of F(t) was learned, and during application, all instances above $1.2 \times \sigma$ were accepted as candidates for cardiac triggers. Because this method may yield a number of spurious candidates, a stationary Poisson point process with intensity $\lambda=0.125$, corresponding 0.8 s, was used to select a single trigger per cycle.

OCM and ECG results were compared for outside and inside the MR bore. Outside, 115 heartbeats were detected by both modalities. Mean heartbeat duration and standard deviation were 958 ms (±57.7 ms) for ECG and 956 ms (±71.6 ms) for OCM. Inside the scanner, these values were 964 ms (±50.6 ms) for ECG and 963 ms (±67.5 ms) for OCM (Figure X). Mean temporal deviation of each OCM trigger compared to its corresponding ECG trigger was −20 ms (±3 ms) outside the scanner, −18 ms (±3 ms), inside the scanner.

The results of this experiment showed a novel approach for cardiac triggering inside the MR bore that is not susceptible to the magnetohydrodynamic effect. The correct number of heartbeats was detected using our approach, as compared to ECG, and detected heartbeat duration proved very similar. A consistent shift between ECG and OCM triggers might indicate a systematic error, possibly due to a synchronization offset of the data streams, or more likely because the R-wave occurs slightly prior to the observable rapid motion of the heart detected by OCM. The present study was aimed at testing equivalence in cases where the ECG R-wave detection works well, future work should be directed at proving superiority in cases where ECG detection does not work well, which happens more frequently at higher field strengths.

The present disclosure has described one or more preferred embodiments, and it should be appreciated that many equivalents, alternatives, variations, and modifications, aside from those expressly stated, are possible and within the scope of the invention.

The invention claimed is:

1. A system for correction of medical imaging data, the system comprising:
    an array of ultrasound sensors, each ultrasound sensor in the array of ultrasound sensors configured to be located at a variety of different spatial locations on a subject being imaged by an imaging system configured to generate medical imaging data and each ultrasound sensor configured to receive ultrasound sensor data;
    a processor configured to:
        receive the ultrasound sensor data from the array of ultrasound sensors;
        multiplex the ultrasound sensor data;
        generate anatomical information from the multiplexed ultrasound sensor data and correlated to the imaging system; and
        deliver the anatomical information to the imaging system to gate acquisition of the imaging data using the anatomical information or to reconstruct the imaging data using the anatomical information.

2. The system of claim 1, further comprising one or more complementary sensors configured to receive complementary data.

3. The system of claim 2, wherein the processor is configured to generate the anatomical information from the complementary data and the ultrasound sensor data.

4. The system of claim 1, wherein the imaging system comprises a magnetic resonance imaging or tomographic imaging system.

5. The system of claim 4, wherein the tomographic imaging system is a computed tomography (CT), positron emission tomography (PET), or a single photon emission computed tomography (SPECT) system.

6. The system of claim 1, wherein the ultrasound sensors are each single element ultrasound transducers.

7. The system of claim 6, wherein the ultrasound sensors comprise individual capsules enclosing the transducers.

8. The system of claim 1, wherein the anatomical information comprises cardiac cycle information of the subject.

9. The system of claim 1, wherein the variety of different spatial locations are positioned on the chest of the subject.

10. The system of claim 1, wherein delivering the anatomical information to the imaging system occurs in real-time.

11. The system of claim 1, wherein the anatomical information comprises respiration-related information of the subject.

* * * * *

UNITED STATES PATENT AND TRADEMARK OFFICE
CERTIFICATE OF CORRECTION

PATENT NO. : 11,744,558 B2
APPLICATION NO. : 16/499660
DATED : September 5, 2023
INVENTOR(S) : Bruno Madore et al.

It is certified that error appears in the above-identified patent and that said Letters Patent is hereby corrected as shown below:

In the Specification

Column 1, Lines 8-12:
"This application claims the benefit of U.S. Provisional Patent Application 62/479,774, filed Mar. 31, 2017, and entitled "MRI Sensors" and U.S. Provisional Patent Application 62/598,561, filed Dec. 14, 2017, and entitled "Ultrasound-based Sensors and Active Needles for Enhanced Medical Imaging and Therapy.""
Should be:
--This application represents the U.S. National Stage Entry of International Application PCT/US2018/025602, filed March 31, 2018; which claims benefit of U.S. Provisional Patent Applications 62/479,774, filed March 31, 2017, and 62/598,561, filed December 14, 2017. All of the above applications are hereby incorporated by reference in their entireties.--.

Column 11, Line 25:
"deviation a of"
Should be;
--deviation σ of--.

Signed and Sealed this
Twenty-first Day of November, 2023

Katherine Kelly Vidal
*Director of the United States Patent and Trademark Office*